US012721685B2

(12) United States Patent
Steinke et al.

(10) Patent No.: US 12,721,685 B2
(45) Date of Patent: Sep. 1, 2026

(54) USE OF EVOKED POTENTIALS IN DEEP BRAIN STIMULATION NEUROMODULATION

(71) Applicant: Boston Scientific Neuromodulation Corporation, Valencia, CA (US)

(72) Inventors: G. Karl Steinke, Valencia, CA (US); Mahsa Malekmohammadi, Sherman Oaks, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 19/071,353

(22) Filed: Mar. 5, 2025

(65) Prior Publication Data

US 2025/0302544 A1 Oct. 2, 2025

Related U.S. Application Data

(60) Provisional application No. 63/570,457, filed on Mar. 27, 2024.

(51) Int. Cl.

| | |
|---|---|
| ***A61N 1/05*** | (2006.01) |
| ***A61B 34/00*** | (2016.01) |
| ***A61B 34/20*** | (2016.01) |
| ***A61N 1/08*** | (2006.01) |
| ***A61N 1/36*** | (2006.01) |
| ***A61N 1/372*** | (2006.01) |

(52) U.S. Cl.
CPC ............. *A61B 34/20* (2016.02); *A61B 34/25* (2016.02); *A61N 1/0534* (2013.01); *A61N 1/08* (2013.01); *A61N 1/36135* (2013.01); *A61N 1/37241* (2013.01); *A61B 2034/2053* (2016.02)

(58) Field of Classification Search
CPC .... A61N 1/0529; A61N 1/0534; A61B 34/20; A61B 2034/2051; A61B 2034/2053
See application file for complete search history.

(56) References Cited

U.S. PATENT DOCUMENTS

| | | | |
|---|---|---|---|
| 6,181,969 | B1 | 1/2001 | Gord |
| 6,845,267 | B2 | 1/2005 | Harrison et al. |
| 6,950,707 | B2 | 9/2005 | Whitehurst |
| 8,606,362 | B2 | 12/2013 | He et al. |
| 8,620,436 | B2 | 12/2013 | Parramon et al. |
| 11,298,070 | B2 | 4/2022 | Sinclair et al. |
| 11,813,458 | B2 | 11/2023 | Esteller et al. |
| 2012/0092031 | A1 | 4/2012 | Shi et al. |
| 2012/0095519 | A1 | 4/2012 | Parramon et al. |

(Continued)

OTHER PUBLICATIONS

International Search Report and Written Opinion Regarding Corresponding PCT Application No. PCT/US2025/018554, mailed May 13, 2025.

*Primary Examiner* — Colin T. Sakamoto
(74) *Attorney, Agent, or Firm* — Lewis & Reese, PLLC

(57) ABSTRACT

Methods and systems for providing deep brain stimulation (DBS) for a patient are described. Electrical stimulation is provided to a patient's brain and evoked potentials (EPs) are recorded at two or more electrodes. The EPs evoked and/or recorded at different electrodes are used to estimate if the respective electrodes are located in the same or different anatomical brain regions. The EPs may also be used to predict or suggest appropriate stimulation rates for therapeutic stimulation.

20 Claims, 11 Drawing Sheets

(56) References Cited

U.S. PATENT DOCUMENTS

| | | | |
|---|---|---|---|
| 2012/0095529 | A1 | 4/2012 | Parramon et al. |
| 2013/0289665 | A1 | 10/2013 | Marnfeldt et al. |
| 2015/0080982 | A1 | 3/2015 | Funderburk |
| 2015/0157861 | A1 | 6/2015 | Aghassian |
| 2015/0231402 | A1 | 8/2015 | Aghassian |
| 2015/0360038 | A1 | 12/2015 | Zottola et al. |
| 2018/0071513 | A1 | 3/2018 | Weiss et al. |
| 2018/0071520 | A1 | 3/2018 | Weerakoon et al. |
| 2018/0071527 | A1 | 3/2018 | Feldman et al. |
| 2018/0140831 | A1 | 5/2018 | Feldman et al. |
| 2018/0221644 | A1 | 8/2018 | Grill et al. |
| 2019/0083796 | A1 | 3/2019 | Weerakoon et al. |
| 2019/0209851 | A1 | 7/2019 | Kothandaraman et al. |
| 2022/0040486 | A1 | 2/2022 | Moffitt |
| 2022/0047872 | A1 | 2/2022 | Ince et al. |
| 2022/0111213 | A1 | 4/2022 | Cassar et al. |
| 2022/0296892 | A1* | 9/2022 | Esteller ................ A61N 1/3614 |
| 2023/0099390 | A1 | 3/2023 | Esteller et al. |
| 2023/0166111 | A1 | 6/2023 | Hageman et al. |

* cited by examiner 50
56a
56b
54
17
Tissue boundary 60
64b
64a
62
66
50
56a
56b
10
27a
27b 76
80b
80a
80b
79
70
74
82
72
88
80b
84
86

USE OF EVOKED POTENTIALS IN DEEP BRAIN STIMULATION NEUROMODULATION

CROSS REFERENCE TO RELATED APPLICATIONS

This is a non-provisional application of U.S. Provisional Patent Application Ser. No. 63/570,457, filed Mar. 27, 2024, which is incorporated herein by reference, and to which priority is claimed.

FIELD OF THE INVENTION

This application relates to deep brain stimulation (DBS), and more particularly, to methods and systems for using sensed neural responses for facilitating aspects of DBS.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) context. DBS has been applied therapeutically for the treatment of neurological disorders, including Parkinson's Disease (PD), essential tremor, dystonia, and epilepsy, to name but a few. Further details discussing the treatment of diseases using DBS are disclosed in U.S. Pat. Nos. 6,845,267, and 6,950,707. However, the present invention may find applicability with any implantable neurostimulator device system.

Each of these neurostimulation systems, whether implantable or external, typically includes one or more electrode-carrying stimulation leads, which are implanted at the desired stimulation site, and a neurostimulator, used externally or implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that may need to be stimulated to provide the therapeutic benefit (e.g., treatment of movement disorders), while minimizing the stimulation of non-target tissue. A typical stimulation parameter set may include the electrodes that are acting as anodes or cathodes, as well as the amplitude, duration, and rate of the stimulation pulses.

Non-optimal electrode placement and stimulation parameter selections may result in excessive energy consumption due to stimulation that is set at too high amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects. For example, bilateral DBS of the subthalamic nucleus (STN) has been shown to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., Reversing Cognitive-Motor Impairments in Parkinson's Disease Patients Using a Computational Modelling Approach to Deep Brain Stimulation Programming, Brain 2010; pp. 1-16). In large part, this phenomenon is due to the small size of the subthalamic nucleus. Even with the electrodes located predominately within the sensorimotor territory, the electrical field generated by DBS is non-discriminately applied to all neural elements surrounding the electrodes, thereby resulting in the spread of current to neural elements affecting cognition. As a result, diminished cognitive function during stimulation of the subthalamic nucleus may occur due to non-selective activation of non-motor pathways within or around the subthalamic nucleus.

The large number of electrodes available, combined with the ability to generate a variety of complex stimulation pulses, presents a huge selection of stimulation parameter sets to the clinician or patient. In the context of DBS, neurostimulation leads with a complex arrangement of electrodes that not only are distributed axially along the leads but are also distributed circumferentially around the neurostimulation leads as segmented electrodes, can be used.

To facilitate such selection, the clinician generally programs the external control device, and if applicable the neurostimulator, through a computerized programming system. This programming system can be a self-contained hardware/software system or can be defined predominantly by software running on a standard personal computer (PC) or mobile platform. The PC or custom hardware may actively control the characteristics of the electrical stimulation generated by the neurostimulator to allow the optimum stimulation parameters to be determined based on patient feedback and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. The system may also instruct the user how to improve the positioning of the leads or confirm when a lead is well-positioned. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

SUMMARY

Disclosed herein is a method of estimating a position of an electrode lead within a patient's brain, wherein the electrode lead comprises a plurality of electrodes, the method comprising: using one or more of the plurality of electrodes to provide active stimulation to the patient's brain; using at least a first of the plurality of electrodes to record first evoked potentials (EPs) evoked by the active stimulation and a second of the plurality of electrodes to record second EPs evoked by the active stimulation; comparing the first EPs and the second EPs; and using the comparison to estimate a location of the electrode lead within the patient's brain. According to some embodiments, the first and second EPs comprise evoked resonant neural responses (ERNA). According to some embodiments, comparing the first and second EPs comprises determining a delay between the EPs. According to some embodiments, the delay is indicative of a difference in a number or kind of synapses between a first neural circuit giving rise to the first EP and a second neural circuit giving rise to the second EP. According to some embodiments, estimating a location of the electrode lead within the patient's brain comprises determining if the first and second electrodes are in different anatomical brain structures. According to some embodiments, the method further comprises taking an action based on the estimated relative or absolution location of the electrode lead within the patient's brain. According to some embodiments, the action comprises moving the electrode lead or suggesting a move of the electrode lead. According to some embodiments, the action comprises suggesting or optimizing an electrode configuration, wherein the electrode configuration comprises one or more of the plurality of electrodes assigned to deliver therapeutic stimulation. According to some embodiments, the action comprises updating a prior estimate of the electrode lead's location within the patient's brain. According to some embodiments, the updating comprises adjusting a location of a graphical representation of the electrode lead with respect to one or more graphical representations of imaging data using a graphical user interface (GUI).

Also disclose herein is a system for estimating a position of an electrode lead within a patient's brain, wherein the electrode lead comprises a plurality of electrodes, the system comprising: control circuitry configured to: use one or more of the plurality of electrodes to provide active stimulation to the patient's brain; use at least a first of the plurality of electrodes to record first evoked potentials (EPs) evoked by the active stimulation and a second of the plurality of electrodes to record second EPs evoked by the active stimulation; compare the first EPs and the second EPs; and use the comparison to estimate a location of the electrode lead within the patient's brain. According to some embodiments, the first and second EPs comprise evoked resonant neural responses (ERNA). According to some embodiments, comparing the first and second EPs comprises determining a delay between the EPs. According to some embodiments, the delay is indicative of a difference in a number or kind of synapses between a first neural circuit giving rise to the first EP and a second neural circuit giving rise to the second EP. According to some embodiments, estimating a location of the electrode lead within the patient's brain comprises determining if the first and second electrodes are in different anatomical brain structures. According to some embodiments, the system is further configured to take an action based on the estimated relative or absolution location of the electrode lead within the patient's brain. According to some embodiments, the action comprises moving the electrode lead or suggesting a move of the electrode lead. According to some embodiments, the action comprises suggesting or optimizing an electrode configuration, wherein the electrode configuration comprises one or more of the plurality of electrodes assigned to deliver therapeutic stimulation. According to some embodiments, the action comprises updating a prior estimate of the electrode lead's location within the patient's brain. According to some embodiments, the updating comprises adjusting a location of a graphical representation of the electrode lead with respect to one or more graphical representations of imaging data using a graphical user interface (GUI).

Also disclosed herein is a method of estimating a position of an electrode lead within a patient's brain, wherein the electrode lead comprises a plurality of electrodes, the method comprising: determining a preliminary estimate of the electrode lead's position within the patient's brain; using one or more of the plurality of electrodes to provide active stimulation to the patient's brain; using at least a first electrode of the plurality of the electrodes to record first evoked potentials (EPs) evoked by the active stimulation and a second electrode of the plurality of the electrodes to record second EPs evoked by the active stimulation; determining a relationship between the first EPs and the second EPs; comparing the determined relationship to a predicted relationship, wherein the predicted relationship is based on the preliminary estimate; and using the comparison to update the preliminary estimate. According to some embodiments, the predicted relationship is based on a prediction of a location of the first electrode in a first anatomical brain structure and a location of the second electrode in a second anatomical brain structure. According to some embodiments, the predicted location of the first and second electrodes is based on imaging data.

Also disclosed herein is a system for estimating a position of an electrode lead within a patient's brain, wherein the electrode lead comprises a plurality of electrodes, the system comprising: control circuitry configured to: determine a preliminary estimate of the electrode lead's position within the patient's brain; use one or more of the plurality of electrodes to provide active stimulation to the patient's brain; use at least a first electrode of the plurality of the electrodes to record first evoked potentials (EPs) evoked by the active stimulation and a second electrode of the plurality of the electrodes to record second EPs evoked by the active stimulation; determine a relationship between the first EPs and the second EPs; compare the determined relationship to a predicted relationship, wherein the predicted relationship is based on the preliminary estimate; and use the comparison to update the preliminary estimate. According to some embodiments, the predicted relationship is based on a prediction of a location of the first electrode in a first anatomical brain structure and a location of the second electrode in a second anatomical brain structure. According to some embodiments, the predicted location of the first and second electrodes is based on imaging data.

Also disclosed herein is a method for determining a rate of therapeutic stimulation to be applied to a patient's brain using an electrode lead within a patient's brain, wherein the electrode lead comprises a plurality of electrodes, the method comprising: using one or more of the plurality of electrodes to provide active stimulation to the patient's brain; using at least one of the plurality of electrodes to record evoked potentials (EPs) evoked by the active stimulation; using the recorded EPs to determine a frequency for therapeutic stimulation to be provided to the patient's brain, and using one or more of the plurality of electrodes to provide the therapeutic stimulation to the patient's brain. According to some embodiments, the EPs comprise evoked resonant neural responses (ERNA). According to some embodiments, using the recorded EPs to determine a frequency for therapeutic stimulation comprises determining a frequency of the recorded EPs. According to some embodiments, determining a frequency for the of the recorded EPs comprises determining one or more of an instantaneous frequency or an average frequency. According to some embodiments, using the recorded EPs to determine a frequency for therapeutic stimulation comprises using a transfer function relating the frequency of the EPs to the frequency of the therapeutic stimulation. According to some embodiments, the transfer function comprises using a predetermined fraction of the frequency of the EPs to provide the frequency of the therapeutic stimulation. According to some embodiments, the predetermined fraction is based on a predicted location of the at least one electrode within a particular anatomical brain structure. According to some embodiments, the method further comprises selecting the predetermined fraction from a plurality of possible predetermined fractions based on the predicted location of the at least one electrode within the particular anatomical brain structure. According to some embodiments, using the recorded EPs to determine a frequency for therapeutic stimulation comprises averaging a plurality of traces of the recorded EPs. According to some embodiments, the plurality of traces is from the same electrode. According to some embodiments, the plurality of traces is from different electrodes. According to some embodiments, the method further comprises selecting the at least one electrode from the plurality of electrodes. According to some embodiments, selecting the at least one electrode comprises determining an amplitude of EPs recorded at each of the plurality of electrodes. According to some embodiments, selecting the at least one electrode comprises determining a frequency of EPs recorded at each of the plurality of electrodes. According to some embodiments, selecting the at least one electrode comprises comparing EPs recorded at each of the plurality of electrodes with an expected EP. According to some embodiments, selecting the at least one electrode comprises determining anatomical brain structure in which each of the plurality of electrodes are located.

Also disclosed herein is a system for determining a rate of therapeutic stimulation to be applied to a patient's brain using an electrode lead within a patient's brain, wherein the electrode lead comprises a plurality of electrodes, the system comprising: control circuitry configured to: use one or more of the plurality of electrodes to provide active stimulation to the patient's brain; use at least one of the plurality of electrodes to record evoked potentials (EPs) evoked by the active stimulation; use the recorded EPs to determine a frequency for therapeutic stimulation to be provided to the patient's brain, and use one or more of the plurality of electrodes to provide the therapeutic stimulation to the patient's brain. According to some embodiments, the EPs comprise evoked resonant neural responses (ERNA). According to some embodiments, using the recorded EPs to determine a frequency for therapeutic stimulation comprises determining a frequency of the recorded EPs. According to some embodiments, determining a frequency for the of the recorded EPs comprises determining one or more of an instantaneous frequency or an average frequency. According to some embodiments, using the recorded EPs to determine a frequency for therapeutic stimulation comprises using a transfer function relating the frequency of the EPs to the frequency of the therapeutic stimulation. According to some embodiments, the transfer function comprises using a predetermined fraction of the frequency of the EPs to provide the frequency of the therapeutic stimulation. According to some embodiments, the predetermined fraction is based on a predicted location of the at least one electrode within a particular anatomical brain structure. According to some embodiments, the system is further configured to select the predetermined fraction from a plurality of possible predetermined fractions based on the predicted location of the at least one electrode within the particular anatomical brain structure. According to some embodiments, using the recorded EPs to determine a frequency for therapeutic stimulation comprises averaging a plurality of traces of the recorded EPs. According to some embodiments, the plurality of traces is from the same electrode. According to some embodiments, the plurality of traces is from different electrodes. According to some embodiments, they system is further configured to select the at least one electrode from the plurality of electrodes. According to some embodiments, selecting the at least one electrode comprises determining an amplitude of EPs recorded at each of the plurality of electrodes. According to some embodiments, selecting the at least one electrode comprises determining a frequency of EPs recorded at each of the plurality of electrodes. According to some embodiments, selecting the at least one electrode comprises comparing EPs recorded at each of the plurality of electrodes with an expected EP. According to some embodiments, selecting the at least one electrode comprises determining anatomical brain structure in which each of the plurality of electrodes are located.

The invention may also reside in the form of a programed external device (via its control circuitry) for carrying out the above methods, a programmed implantable pulse generator (IPG) or external trial stimulator (ETS), external pulse generator (EPG), or operating room stimulator (OR stimulator, or "OR box") (via their respective control circuitry) for carrying out the above methods, a system including a programmed external device and IPG or ETS for carrying out the above methods, or as a computer-readable media for carrying out the above methods stored in an external device or IPG or ETS. The invention may also reside in one or more non-transitory computer-readable media comprising instructions, which when executed by a processor of a machine configure the machine to perform any of the above methods.

DETAILED DESCRIPTION

Figure 1A:
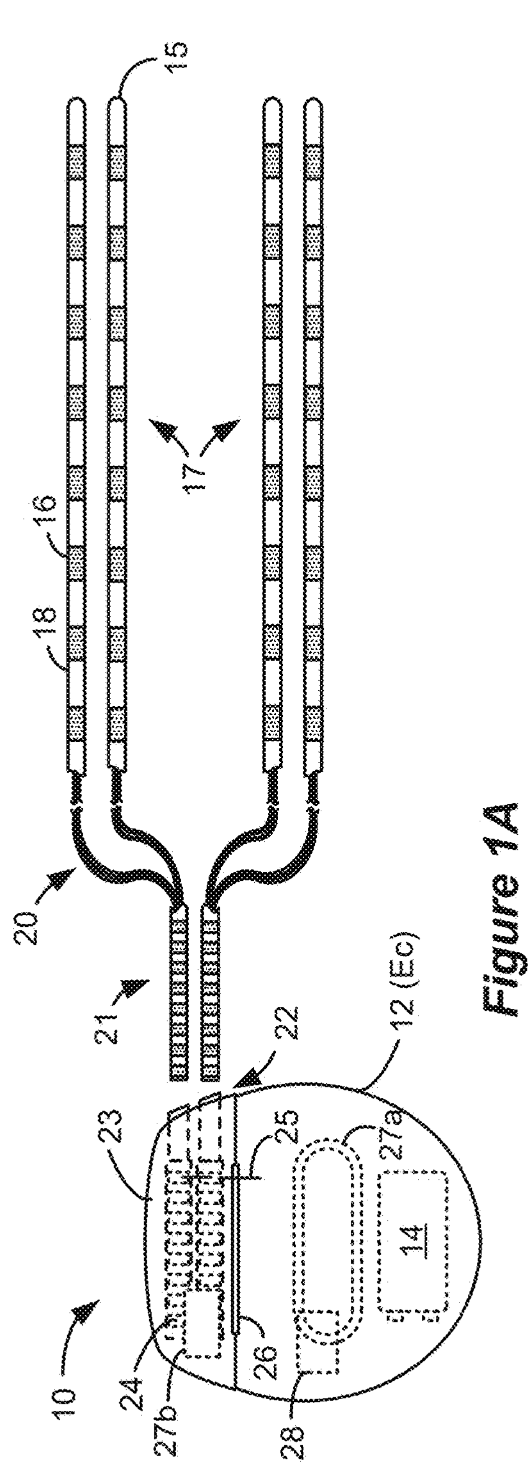
FIGS. 1A and 1B show an Implantable Pulse Generator (IPG) and electrode lead having split-ring electrodes, respectively.

A DBS or SCS system typically includes an Implantable Pulse Generator (IPG) 10 shown in FIG. 1A. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more electrode leads 15 can be used having ring-shaped electrodes 16 carried on a flexible body 18.

Figure 1B:
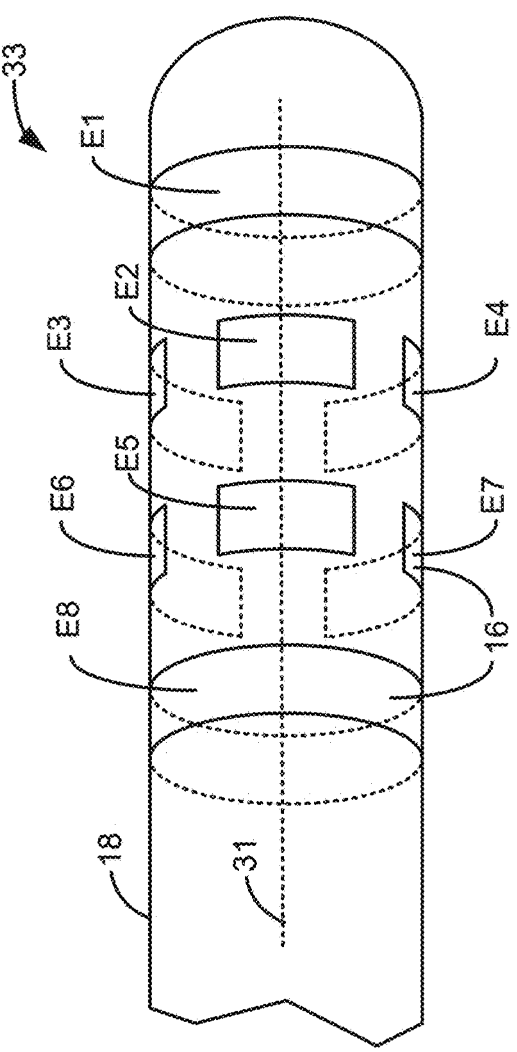

In yet another example shown in FIG. 1B, an electrode lead 33 can include one or more split-ring electrodes. In this example, eight electrodes 16 (E1-E8) are shown. Electrode E1 at the distal end of the lead and electrode E8 at a proximal end of the lead comprise ring electrodes spanning 360 degrees around a central axis of the lead 33. In some embodiments, the electrode E1 may be a "bullet tip" electrode, meaning that it can cover the tip of the electrode lead. Electrodes E2, E3, and E4 comprise split-ring electrodes, each of which are located at the same longitudinal position along the central axis 31, but with each spanning less than 360 degrees around the axis. For example, each of electrodes E2, E3, and E4 may span 90 degrees around the axis 31, with each being separated from the others by gaps of 30 degrees. Electrodes E5, E6, and E7 also comprise split-ring electrodes, but are located at a different longitudinal position along the central axis 31 than are split ring electrodes E4, E2, and E3. As shown, the split-ring electrodes E2-E4 and E5-E7 may be located at longitudinal positions along the axis 31 between ring electrodes E1 and E8. However, this is just one example of a lead 33 having split-ring electrodes. In other designs, all electrodes can be split-ring, or there could be different numbers of split-ring electrodes at each longitudinal position (i.e., more or less than three), or the ring and split-ring electrodes could occur at different or random longitudinal positions, etc.

Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are thirty-two electrodes (E1-E32), split between four percutaneous leads 15, and thus the header 23 may include a 2×2 array of eight-electrode lead connectors 22. However, the type and number of leads, and the number of electrodes, in an IPG is application-specific and therefore can vary. The conductive case 12 can also comprise an electrode (Ec).

In a DBS application, as is useful in the treatment of tremor in Parkinson's disease for example, the IPG 10 is typically implanted under the patient's clavicle (collarbone). Lead wires 20 are tunneled through the neck and the scalp and the electrode leads 15 (or 33) are implanted through holes drilled in the skull and positioned in the patient's brain.

IPG 10 can include an antenna 27*a* allowing it to communicate bi-directionally with a number of external devices discussed subsequently. Antenna 27*a* as shown comprises a conductive coil within the case 12, although the coil antenna 27*a* can also appear in the header 23. When antenna 27*a* is configured as a coil, communication with external devices preferably occurs using near-field magnetic induction. IPG 10 may also include a Radio-Frequency (RF) antenna 27*b*. In FIG. 1A, RF antenna 27*b* is shown within the header 23, but it may also be within the case 12. RF antenna 27*b* may comprise a patch, slot, or wire, and may operate as a monopole or dipole. RF antenna 27*b* preferably communicates using far-field electromagnetic waves, and may operate in accordance with any number of known RF communication standards, such as Bluetooth, Bluetooth Low Energy (BLE), as described in U.S. Patent Publication 2019/0209851, Zigbee, WiFi, MICS, and the like.

Figures 2A, 2B, 3:
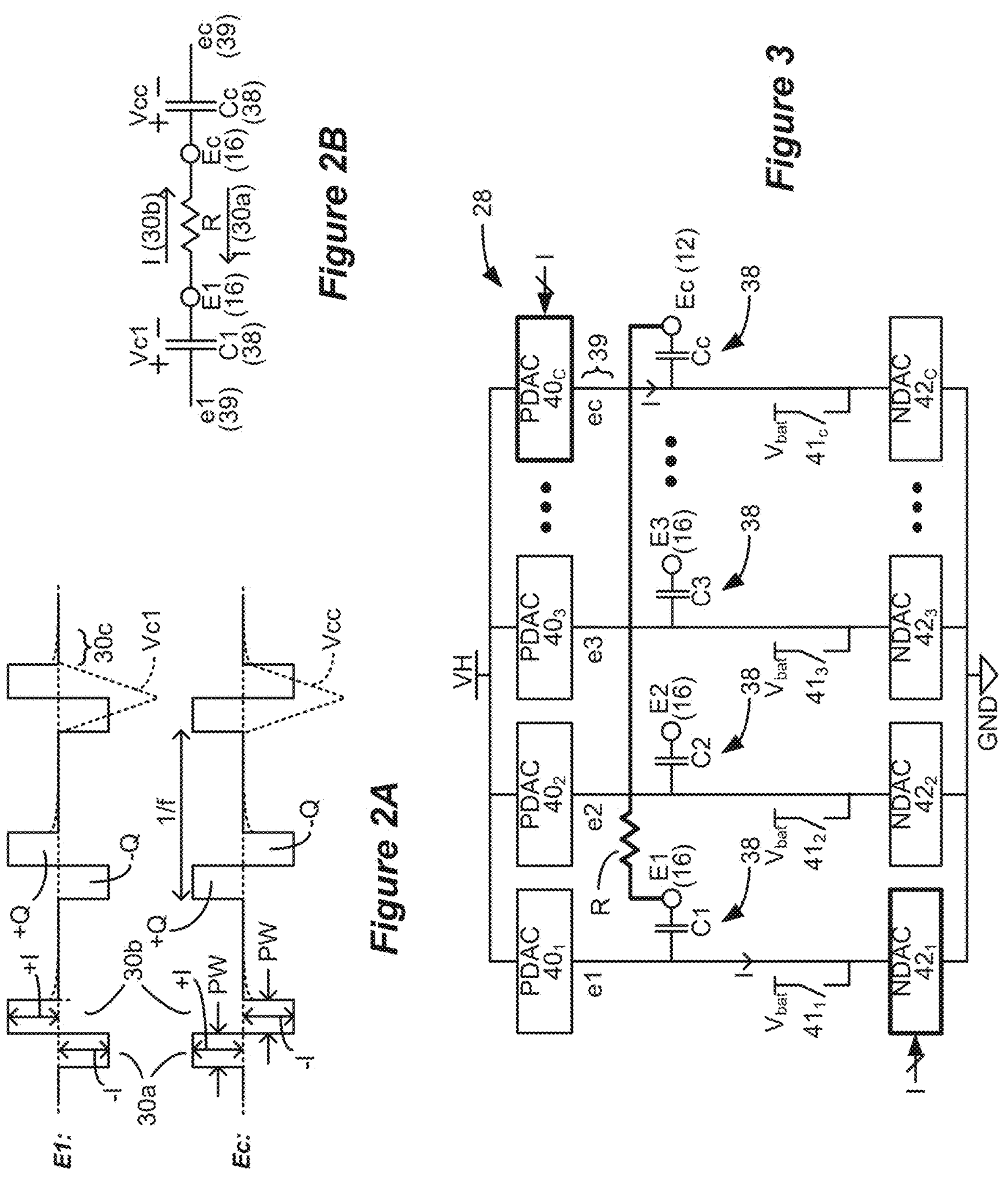
FIGS. 2A and 2B show an example of stimulation pulses (waveforms) producible by the IPG or by an External Trial Stimulator (ETS).
FIG. 3 shows an example of stimulation circuitry useable in the IPG or ETS.

Stimulation in IPG 10 is typically provided by pulses each of which may include a number of phases such as 30*a* and 30*b*, as shown in the example of FIG. 2A. In the example shown, such stimulation is monopolar, meaning that a current is provided between at least one selected lead-based electrode (e.g., E1) and the case electrode Ec 12. Stimulation parameters typically include amplitude (current I, although a voltage amplitude V can also be used); frequency (f); pulse width (PW) of the pulses or of its individual phases such as 30*a* and 30*b*; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30*a*), and thus provides pulses which sink a negative current of amplitude −I from the tissue. The case electrode Ec has been selected as an anode (again during first phase 30*a*), and thus provides pulses which source a corresponding positive current of amplitude +I to the tissue. Note that at any time the current sunk from the tissue (e.g., −I at E1 during phase 30*a*) equals the current sourced to the tissue (e.g., +I at Ec during phase 30*a*) to ensure that the net current injected into the tissue is zero. The polarity of the currents at these electrodes can be changed: Ec can be selected as a cathode, and E1 can be selected as an anode, etc.

IPG 10 as mentioned includes stimulation circuitry 28 to form prescribed stimulation at a patient's tissue. FIG. 3 shows an example of stimulation circuitry 28, which includes one or more current sources $\mathbf{40}_i$ and one or more current sinks $\mathbf{42}_i$. The sources and sinks $\mathbf{40}_i$ and $\mathbf{42}_i$ can comprise Digital-to-Analog converters (DACs), and may be referred to as PDACs $\mathbf{40}_i$ and NDACs $\mathbf{42}_i$ in accordance with the Positive (sourced, anodic) and Negative (sunk, cathodic) currents they respectively issue. In the example shown, a NDAC/PDAC $\mathbf{40}_i/\mathbf{42}_i$ pair is dedicated (hardwired) to a particular electrode node ei 39. Each electrode node Ei 39 is connected to an electrode Ei 16 via a DC-blocking capacitor Ci 38, for the reasons explained below. PDACs 40$_i$ and NDACs 42$_i$ can also comprise voltage sources.

Proper control of the PDACs 40$_i$ and NDACs 42$_i$ allows any of the electrodes 16 and the case electrode Ec 12 to act as anodes or cathodes to create a current through a patient's tissue, R, hopefully with good therapeutic effect. In the example shown, and consistent with the first pulse phase 30*a* of FIG. 2A, electrode E1 has been selected as a cathode electrode to sink current from the tissue R and case electrode Ec has been selected as an anode electrode to source current to the tissue R. Thus, PDAC 40$_C$ and NDAC 42$_1$ are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. Patent Application Publication 2013/0289665.

Other stimulation circuitries 28 can also be used in the IPG 10. In an example not shown, a switching matrix can intervene between the one or more PDACs 40$_i$ and the electrode nodes ei 39, and between the one or more NDACs 42$_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publications 2018/0071520 and 2019/0083796. The stimulation circuitries described herein provide multiple independent current control (MICC) (or multiple independent voltage control) to guide the estimate of current fractionalization among multiple electrodes and estimate a total amplitude that provide a desired strength. In other words, the total anodic (or cathodic) current can be split among two or more electrodes and/or the total cathodic current can be split among two or more electrodes, allowing the stimulation location and resulting field shapes to be adjusted. For example, a "virtual electrode" may be created at a position between two physical electrodes by fractionating current between the two electrodes.

Much of the stimulation circuitry 28 of FIG. 3, including the PDACs 40$_i$ and NDACs 42$_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27*a* and/or 27*b*), circuitry for generating the compliance voltage VH, various measurement circuits, etc.

Also shown in FIG. 3 are DC-blocking capacitors Ci 38 placed in series in the electrode current paths between each of the electrode nodes $e_i$ 39 and the electrodes $E_i$ 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30*a* followed thereafter by a second phase 30*b* of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30*a*, charge will build up across the DC-blocking capacitors C1 and Cc associated with the electrodes E1 and Ec used to produce the current, giving rise to voltages Vc1 and Vcc which decrease in accordance with the amplitude of the current and the capacitance of the capacitors 38 (dV/dt=I/C). During the second pulse phase 30*b*, when the polarity of the current I is reversed at the selected electrodes E1 and Ec, the stored charge on capacitors C1 and Cc is actively recovered, and thus voltages Vc1 and Vcc increase and return to 0V at the end of the second pulse phase 30*b*.

To recover all charge by the end of the second pulse phase 30*b* of each pulse (Vc1=Vcc=0V), the first and second phases 30*a* and 30*b* are charged balanced at each electrode, with the first pulse phase 30*a* providing a charge of −Q(−I*PW) and the second pulse phase 30*b* providing a charge of +Q(+I*PW) at electrode E1, and with the first pulse phase 30*a* providing a charge of +Q and the second pulse phase 30*b* providing a charge of −Q at the case electrode Ec. In the example shown, such charge balancing is achieved by using the same pulse width (PW) and the same amplitude (|I|) for each of the opposite-polarity pulse phases 30*a* and 30*b*. However, the pulse phases 30*a* and 30*b* may also be charged balanced at each electrode if the product of the amplitude and pulse widths of the two phases 30*a* and 30*b* are equal, or if the area under each of the phases is equal, as is known.

FIG. 3 shows that stimulation circuitry 28 can include passive recovery switches 41$_i$, which are described further in U.S. Patent Application Publications 2018/0071527 and 2018/0140831. Passive recovery switches 41$_i$ may be attached to each of the electrode nodes ei 39, and are used to passively recover any charge remaining on the DC-blocking capacitors Ci 38 after issuance of the second pulse phase 30*b*—i.e., to recover charge without actively driving a current using the DAC circuitry. Passive charge recovery can be prudent, because non-idealities in the stimulation circuitry 28 may lead to pulse phases 30*a* and 30*b* that are not perfectly charge balanced.

Therefore, and as shown in FIG. 2A, passive charge recovery typically occurs after the issuance of second pulse phases 30*b*, for example during at least a portion 30*c* of the quiet periods between the pulses, by closing passive recovery switches 41$_i$. As shown in FIG. 3, the other end of the switches 41$_i$ not coupled to the electrode nodes ei 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 by placing the capacitors in parallel between the reference voltage (Vbat) and the patient's tissue. Note that passive charge recovery is illustrated as small exponentially decaying curves during 30*c* in FIG. 2A, which may be positive or negative depending on whether pulse phase 30*a* or 30*b* have a predominance of charge at a given electrode.

Passive charge recovery 30*c* may alleviate the need to use biphasic pulses for charge recovery, especially in the DBS context when the amplitudes of currents may be lower, and therefore charge recovery is less of a concern. For example, and although not shown in FIG. 2A, the pulses provided to the tissue may be monophasic, comprising only a first pulse phase 30*a*. This may be followed thereafter by passive charge recovery 30*c* to eliminate any charge build up that occurred during the singular pulses 30*a*.

Figures 4, 5:
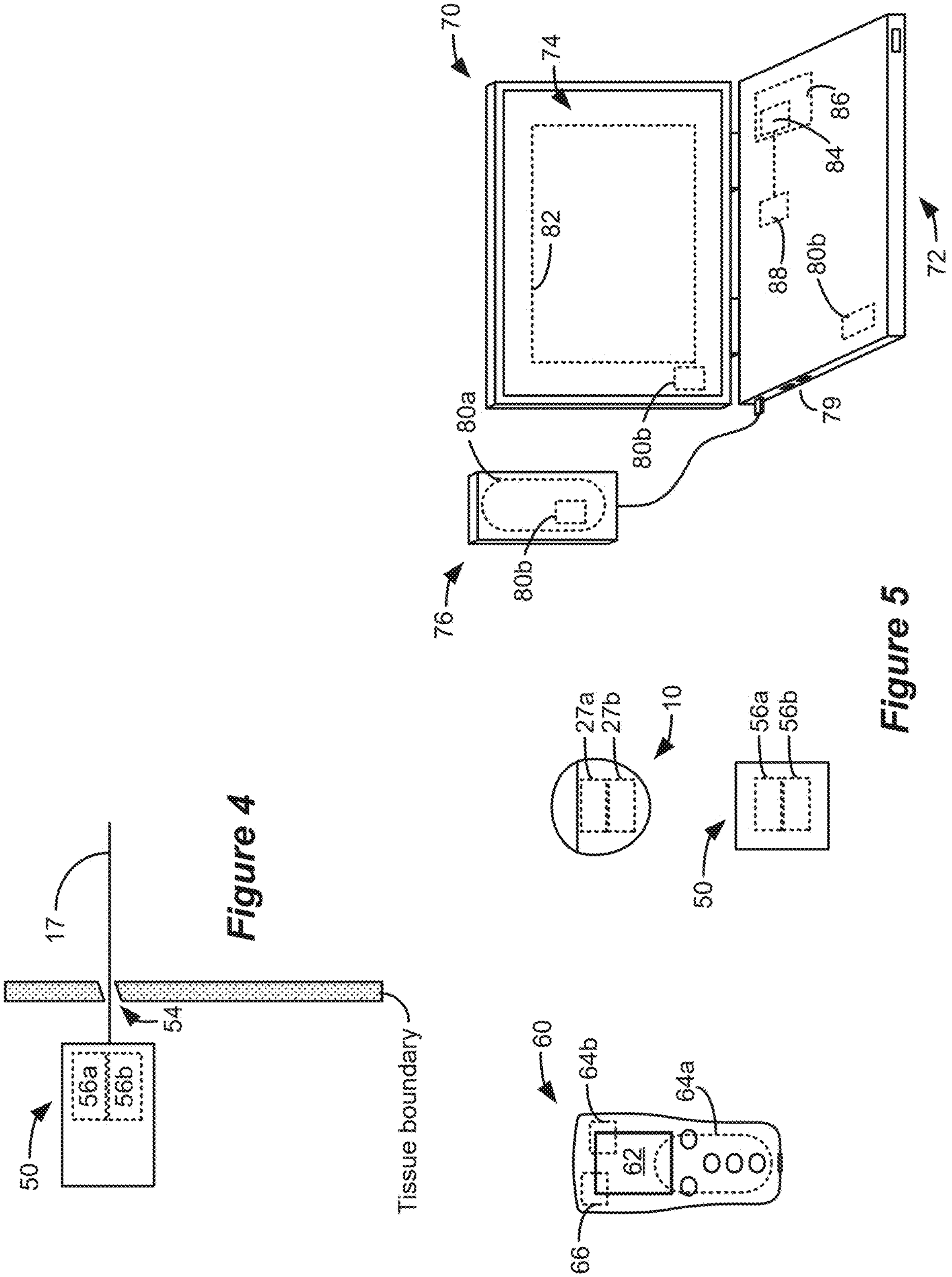
FIG. 4 shows an ETS environment used to provide stimulation before implantation of an IPG.
FIG. 5 shows various external devices capable of communicating with and programming stimulation in an IPG or ETS.

FIG. 4 shows an external trial stimulation environment that may precede implantation of an IPG 10 in a patient, for example, during the operating room to test stimulation and confirm the lead position. During external trial stimulation, stimulation can be tried on the implant patient to evaluate lead implantation and positioning, side-effect thresholds, and confirm that the lead is not too close to structures that cause side effects. An external trial stimulator (ETS) 50 may be used. As used herein, the term "ETS" refers to an external apparatus that comprises control circuitry, stimulation circuitry, and/or sensing circuitry and may be configured to cause the electrode lead 17 to provide stimulation and/or to sense electrical signals within the patient's brain. The term "ETS" may refer to devices that are also called external pulse generators (EPG), operating room stimulators (OR stimulators), operating room boxes (OR boxes), and the like. The ETS may also include electrodes separate from the lead and/or case (patch, needle, etc.) for the purposes of sensing, including channels dedicated to measuring or applying voltages or currents for the purposes of forming a ground or central potential or sensing reference (BIAS), and channels for making single or double ended current or voltage signal measurements (SENSE+, SENSE−), and separate or combined with these, channels for addressing artifact or offset in measurement (offset compensation +/−). Like the IPG 10, the ETS 50 can include one or more antennas to enable bi-directional communications with external devices such as those shown in FIG. 5. Such antennas can include a near-field magnetic-induction coil antenna 56*a*, and/or a far-field RF antenna 56*b*, as described earlier. ETS 50 may also include stimulation circuitry able to form stimulation in accordance with a stimulation program, which circuitry may be similar to or comprise the same stimulation circuitry 28 (FIG. 3) present in the IPG 10. ETS 50 may also include a battery (not shown) for operational power. The sensing capabilities described herein with regard to the IPG 10, may also be included in the ETS 50 for the purposes described below. As the IPG may include a case electrode, an ETS may provide one or more connections to establish similar returns; for example, using patch electrodes. Likewise, the ETS may communicate with the clinician programmer (CP) so that the CP can process the data as described below.

FIG. 5 shows various external devices that can wirelessly communicate data with the IPG 10 or ETS 50, including a patient hand-held external controller 60, and a clinician programmer (CP) 70. Both devices 60 and 70 can be used to wirelessly transmit a stimulation program to the IPG 10 or ETS 50—that is, to program their stimulation circuitries to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10 or ETS 50, such as various status information, etc.

External controller 60 can be as described in U.S. Patent Application Publication 2015/0080982 for example and may comprise a controller dedicated to work with the IPG 10 or ETS 50. External controller 60 may also comprise a general-purpose mobile electronics device such as a mobile phone which has been programmed with a Medical Device Application (MDA) allowing it to work as a wireless controller for the IPG 10 or ETS, as described in U.S. Patent Application Publication 2015/0231402. External controller 60 includes a user interface, preferably including means for entering commands (e.g., buttons or selectable graphical elements) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64*a* capable of wirelessly communicating with the coil antenna 27*a* or 56*a* in the IPG 10 or ETS 50. The external controller 60 can also have a far-field RF antenna 64*b* capable of wirelessly communicating with the RF antenna 27*b* or 56*b* in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27*a* or 56*a*, wand 76 can likewise include a coil antenna 80*a* to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27*b* or 56*b*, the wand 76, the computing device 72, or both, can likewise include an RF antenna 80*b* to establish communication at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at https://www.intel.com/content/www/us/en/products/processors/core/i5-processors.html. Such control circuitry 88, in addition to executing the clinician programmer software 84 and rendering the GUI 82, can also enable communications via antennas 80*a* or 80*b* to communicate stimulation parameters chosen through the GUI 82 to the patient's IPG 10.

The user interface of the external controller 60 may provide similar functionality because the external controller 60 can include similar hardware and software programming as the clinician programmer. For example, the external controller 60 includes control circuitry 66 similar to the control circuitry 88 in the clinician programmer 70 and may similarly be programmed with external controller software stored in device memory.

Figure 6:
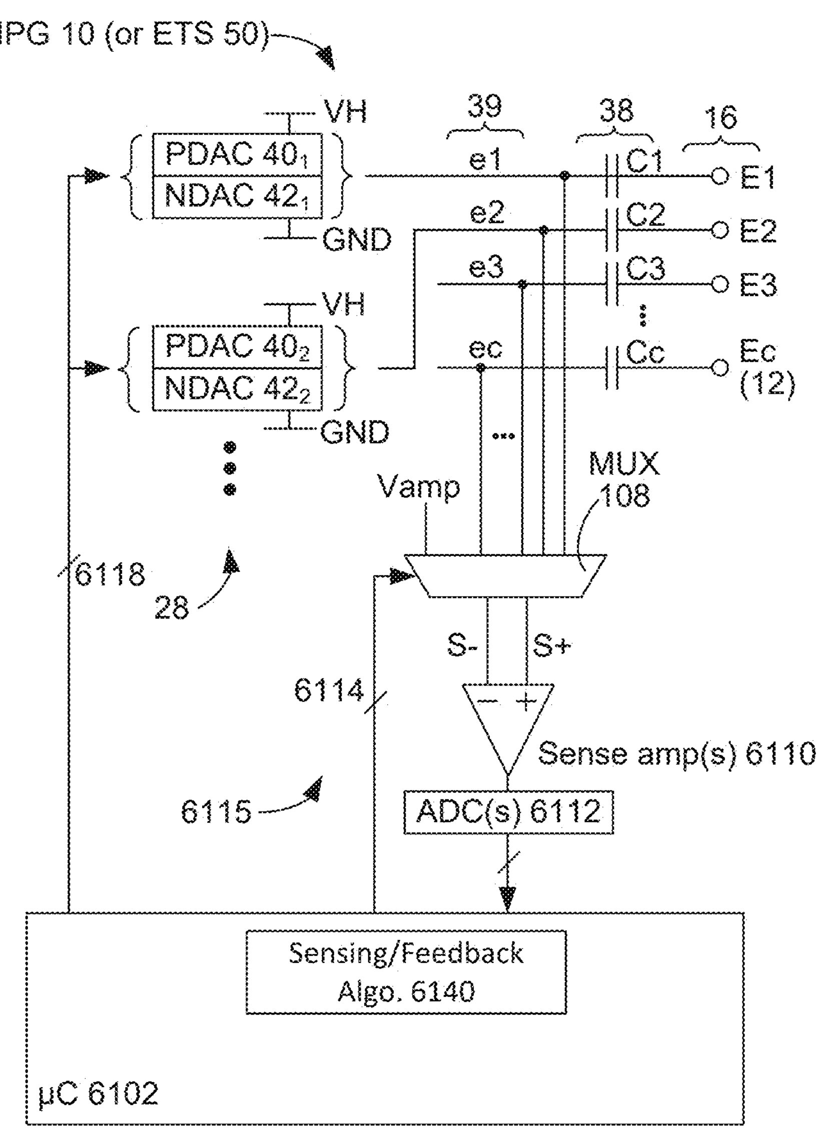
FIG. 6 illustrates sensing circuitry useable in an IPG.

FIG. 6 shows an IPG 10 that includes stimulation and sensing functionality. (An ETS as described earlier could also include stimulation and sensing capabilities). FIG. 6 shows further details of the circuitry in an IPG 10 (and/or ETS) that can provide stimulation and sensing innate or evoked signals. The IPG 10 includes control circuitry 6102, which may comprise a microcontroller, such as Part Number MSP430, manufactured by Texas Instruments, Inc., which is described in data sheets at http://www.ti.com/microcontrollers/msp430-ultra-low-power-mcus/overview.html, which are incorporated herein by reference. Other types of controller circuitry may be used in lieu of a microcontroller as well, such as microprocessors, FPGAs, DSPs, or combinations of these, etc. Control circuitry 6102 may also be formed in whole or in part in one or more Application Specific Integrated Circuits (ASICs), such as those described and incorporated earlier. The control circuitry 102 may be configured with one or more sensing/feedback algorithms 6140 that are configured to cause the IPG/ETS to sense neural signals and make certain adjustments and/or take certain actions based on the sensed neural signals. The sensing/feedback control algorithms may be configured within memory of the IPG.

The IPG 10 also includes stimulation circuitry 28 to produce stimulation at the electrodes 16, which may comprise the stimulation circuitry 28 shown earlier (FIG. 3). A bus 6118 provides digital control signals from the control circuitry 6102 to one or more PDACs $\mathbf{40}_i$ or NDACs $\mathbf{42}_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $\mathbf{41}_i$ (FIG. 3) could also be present but are not shown in FIG. 6 for simplicity.

IPG 10 also includes sensing circuitry 6115, and one or more of the electrodes 16 can be used to sense innate or evoked electrical signals, e.g., biopotentials from the patient's tissue. In this regard, each electrode node 39 can further be coupled to a sense amp circuit 6110. Under control by bus 6114, a multiplexer 6108 can select one or more electrodes to operate as sensing electrodes (S+, S−) by coupling the electrode(s) to the sense amps circuit 6110 at a given time, as explained further below. Although only one multiplexer 6108 and sense amp circuit 6110 are shown in FIG. 6, there could be more than one. For example, there can be four multiplexer 6108/sense amp circuit 6110 pairs each operable within one of four timing channels supported by the IPG 10 to provide stimulation. The sensed signals output by the sense amp circuitry are preferably converted to digital signals by one or more Analog-to-Digital converters (ADC(s)) 6112, which may sample the output of the sense amp circuit 6110 at 50 kHz for example. The ADC(s) 6112 may also reside within the control circuitry 6102, particularly if the control circuitry 6102 has A/D inputs. Multiplexer 6108 can also provide a fixed reference voltage, Vamp, to the sense amp circuit 6110, as is useful in a single-ended sensing mode (i.e., to set S− to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the signals being sensed will still readily be sensed by the sense amp circuitry 6110. In other examples, signals may be sensed directly at the electrodes 16 without passage through intervening capacitors 38.

According to some embodiments, it may be preferred to sense signals differentially, and in this regard, the sense amp circuitry 6110 comprises a differential amplifier receiving the sensed signal S+ (e.g., E3) at its non-inverting input and the sensing reference S− (e.g., E1) at its inverting input. As one skilled in the art understands, the differential amplifier will subtract S− from S+ at its output, and so will cancel out any common mode voltage from both inputs. This can be useful for example when sensing various neural signals, as it may be useful to subtract the relatively large-scale stimulation artifact from the measurement (as much as possible).

Figure 7:
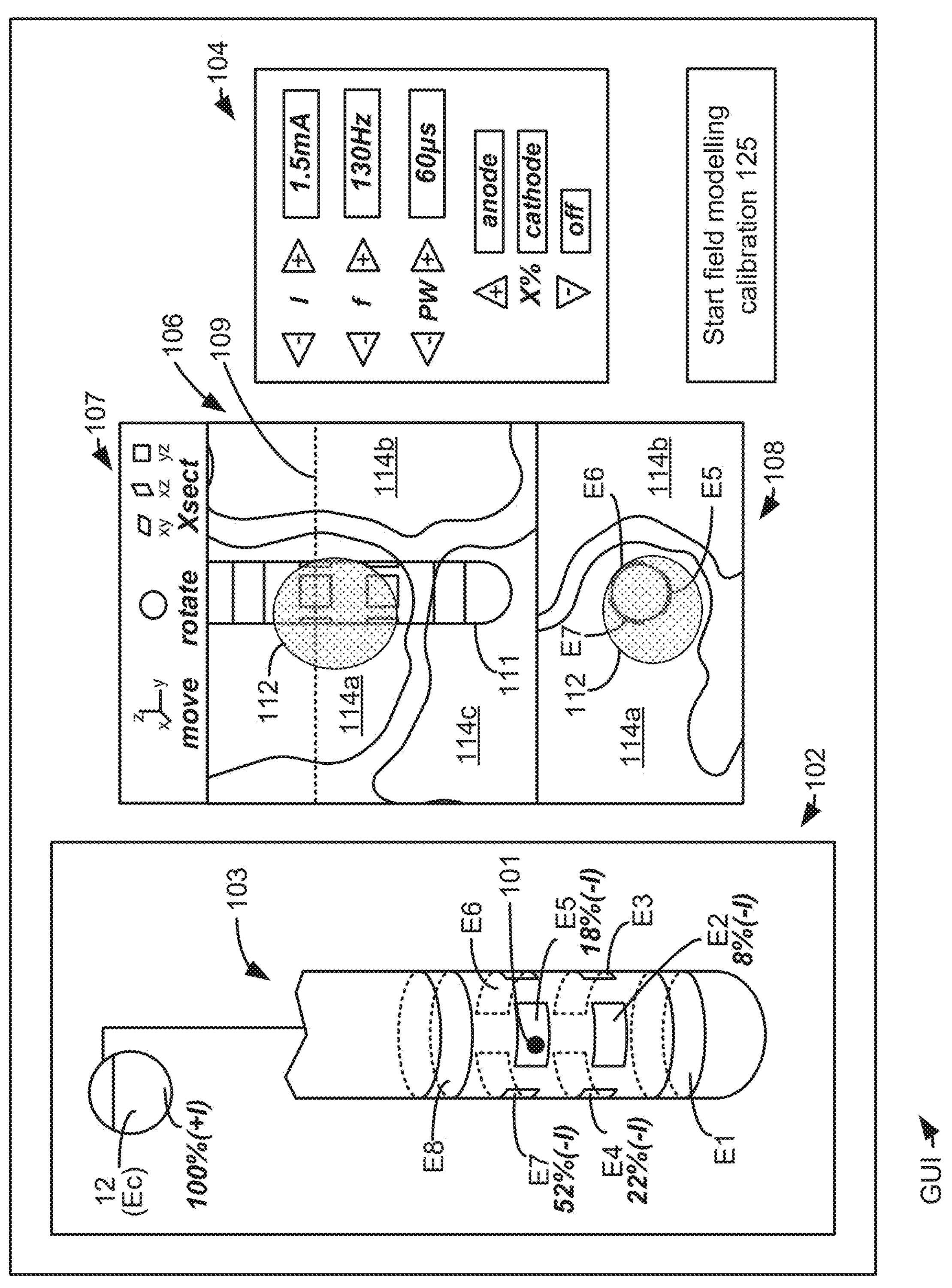
FIG. 7 illustrates an embodiment of a user interface (UI) for programming stimulation.

Particularly in the DBS context, it can be useful to provide a clinician with a visual indication of how stimulation selected for a patient will interact with the tissue in which the electrodes are implanted. This is illustrated in FIG. 7, which shows a Graphical User Interface (GUI) 100 operable on an external device capable of communicating with an IPG 10 or ETS 50. Typically, and as assumed in the description that follows, GUI 100 would be rendered on a clinician programmer 70 (FIG. 5), which may be used during surgical implantation of the leads to inform lead placement, or after implantation when a therapeutically useful stimulation program is being chosen for a patient. However, GUI 100 could be rendered on a patient external programmer 60 (FIG. 5) or any other external device capable of communicating with the IPG 10 or ETS 50.

GUI 100 allows a clinician (or patient) to select the stimulation program that the IPG 110 or ETS 50 will provide and provides options that control sensing of innate or evoked responses, as described below. In this regard, the GUI 100 may include a stimulation parameter interface 104 where various aspects of the stimulation program can be selected or adjusted. For example, interface 104 allows a user to select the amplitude (e.g., a current I) for stimulation; the frequency (f) of stimulation pulses; and the pulse width (PW) of the stimulation pulses. Stimulation parameter interface 104 can be significantly more complicated, particularly if the IPG 10 or ETS 50 supports the provision of stimulation that is more complicated than a repeating sequence of pulses. See, e.g., U.S. Patent Application Publication 2018/0071513. Nonetheless, interface 104 is simply shown for simplicity in FIG. 7 as allowing only for amplitude, frequency, and pulse width adjustment. Stimulation parameter interface 104 may include inputs to allow a user to select whether stimulation will be provided using biphasic (FIG. 2A) or monophasic pulses, and to select whether passive charge recovery will be used, although again these details aren't shown for simplicity.

Stimulation parameter interface 104 may further allow a user to select the active electrodes—i.e., the electrodes that will receive the prescribed pulses. Selection of the active electrodes can occur in conjunction with a leads interface 102, which can include an image 103 of the one or more leads that have been implanted in the patient. Although not shown, the leads interface 102 can include a selection to access a library of relevant images 103 of the types of leads that may be implanted in different patients.

In the example shown in FIG. 7, the leads interface 102 shows an image 103 of a single split-ring lead 33 like that described earlier with respect to FIG. 1B. The leads interface 102 can include a cursor 101 that the user can move (e.g., using a mouse connected to the clinician programmer 70) to select an illustrated electrode 16 (e.g., E1-E8, or the case electrode Ec). Once an electrode has been selected, the stimulation parameter interface 104 can be used to designate the selected electrode as an anode that will source current to the tissue, or as a cathode that will sink current from the tissue. Further, the stimulation parameter interface 104 allows the amount of the total anodic or cathodic current +I or −I that each selected electrode will receive to be specified in terms of a percentage, X. For example, in FIG. 7, the case electrode 12 Ec is specified to receive X=100% of the current I as an anodic current +I. The corresponding cathodic current −I is split between electrodes E5 (0.18*−I), E7 (0.52*−I), E2 (0.08*−I), and E4 (0.22*−I). Thus, two or more electrodes can be chosen to act as anodes or cathodes at a given time using MICC (as described above), allowing the electric field in the tissue to be shaped. The currents specified at the selected electrodes can be those provided during a first pulse phase (if biphasic pulses are used), or during an only pulse phase (if monophasic pulses are used).

GUI 100 can further include a visualization interface 106 that can allow a user to view an indication of the effects of stimulation, such as a stimulation field model (SFM) 112 (also referred to as a volume of tissue activated (VTA)) formed using the selected stimulation parameters. The SFM 112 is formed by field modelling, for example, in the clinician programmer 70. The illustrated embodiment of the GUI 99 includes a selection option 125 for initiating such modeling. Only one lead is shown in the visualization interface 106 for simplicity, although again a given patient might be implanted with more than one lead. Visualization interface 106 provides an image 111 of the lead(s) which may be three-dimensional.

The visualization interface 106 preferably, but not necessarily, further includes tissue imaging information 114 taken from the patient, represented as three different tissue structures 114*a*, 114*b* and 114*c* in FIG. 7 for the patient in question, which tissue structures may comprise different areas of the brain for example. Such tissue imaging information may comprise a Magnetic Resonance Image (MRI), a Computed Tomography (CT) image or other type of image. Often, one or more images, such as an MRI, CT, and/or a brain atlas are scaled and combined in a single image model. This allows the clinician programmer 70 on which GUI 100 is rendered to overlay the lead image 111 and the SFM 112 with the tissue imaging information in the visualization interface 106 so that the position of the SFM 112 relative to the various tissue structures 114*i* can be visualized. The image of the patient's tissue may also be taken after implantation of the lead(s), or tissue imaging information may comprise a generic image pulled from a library which is not specific to the patient in question, in some embodiments.

The various images shown in the visualization interface 106 (i.e., the lead image 111, the SFM 112, and the tissue structures 114*i*) can be three-dimensional in nature, and hence may be rendered in the visualization interface 106 in a manner to allow such three-dimensionality to be better appreciated by the user, such as by shading or coloring the images, etc. Additionally, a view adjustment interface 107 may allow the user to move or rotate the images, using cursor 101 for example.

GUI 100 can further include a cross-section interface 108 to allow the various images to be seen in a two-dimensional cross section. Specifically, cross-section interface 108 shows a particular cross section 109 taken perpendicularly to the lead image 111 and through split-ring electrodes E5, E6, and E7. This cross section 109 can also be shown in the visualization interface 106, and the view adjustment interface 107 can include controls to allow the user to specify the plane of the cross section 109 (e.g., in XY, XZ, or YZ planes) and to move its location in the image. Once the location and orientation of the cross section 109 is defined, the cross-section interface 108 can show additional details. For example, the SFM 112 can allow the user to get a sense of the strength and reach of the stimulation at different locations. Although GUI 100 includes stimulation definition (102, 104) and imaging (108, 106) in a single screen of the GUI, these aspects can also be separated as part of the GUI 100 and made accessible through various menu selections, etc.

Especially in a DBS application, it is important that correct stimulation parameters be determined for a given patient. Improper stimulation parameters may not yield effective relief of a patient's symptoms or may cause unwanted side effects. To determine proper stimulation, a clinician typically uses a GUI such as GUI 100 to try different combinations of stimulation parameters. This may occur, at least in part, during a DBS patient's surgery when the leads are being implanted. Such intra-operative determination of stimulation parameters can be useful to determine a general efficacy of DBS therapy. However, finalizing stimulation parameters that are appropriate for a given DBS patient typically occurs after surgery after the patient has had a chance to heal, and after the position of the leads stabilize in the patient. Thus, the patient will typically present to the clinician's office to determine (or further refine) optimal stimulation parameters during a programming session, often referred to as a "fitting session."

Gauging the effectiveness of a given set of stimulation parameters typically involves programming the IPG 10 with that set, and then reviewing the therapeutic effectiveness and side effects that result. Therapeutic effectiveness and side effects are often assessed by one or more different scores(S) for one or more different clinical responses, which are entered into the GUI 99 of the clinician programmer 70 where they are stored with the stimulation parameters set being assessed. Such scores can be subjective in nature, based on patient or clinician observations. For example, bradykinesia (slowness of movement), rigidity, tremor, or other symptoms or side effects, can be scored by the patient, or by the clinician upon observing or questioning the patient. Such scores in one example can range from 0 (best) to 4 (worst). Scores can also be objective in nature based on measurements taken regarding a patient's symptoms or side effects. For example, a Parkinson's patient may be fitted with a wearable sensor that measures tremors, such as by measuring the frequency and amplitude of such tremors. A wearable sensor may communicate such metrics back to the GUI 99, and if necessary, converted to a score.

Figure 8A:
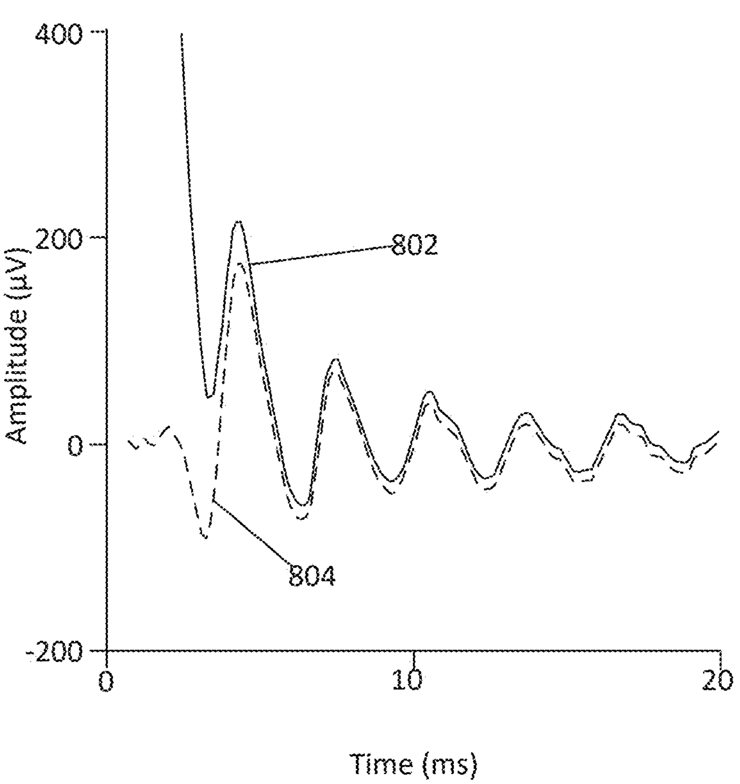
FIGS. 8A and 8B illustrate evoked resonant neural activity (ERNA).
Figure 8B:
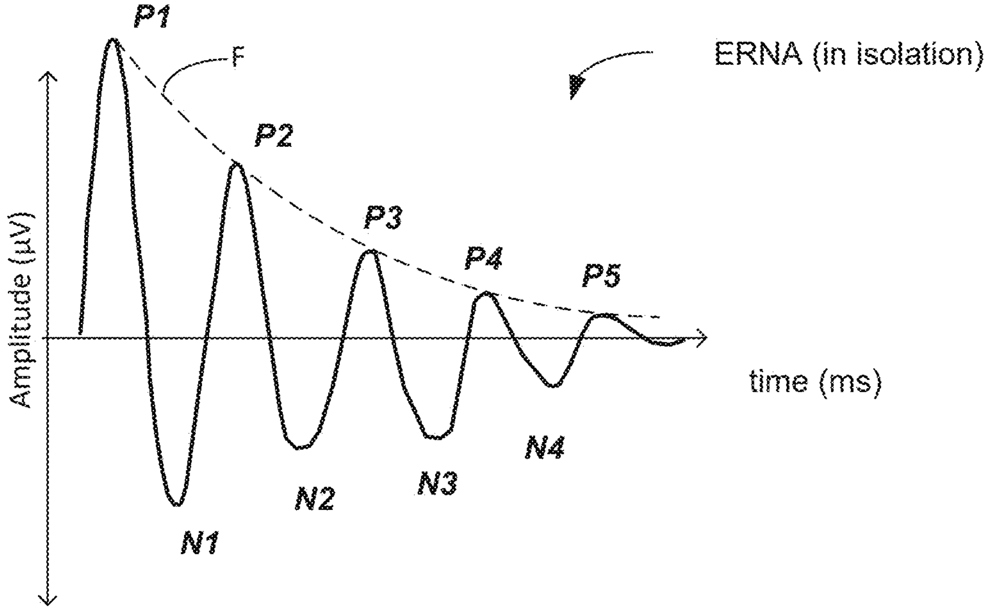

It has been observed that DBS stimulation in certain positions in the brain can evoke neural responses, i.e., electrical activity from neural elements, which may be measured. One example of such neural responses are resonant neural responses, referred to herein as evoked resonant neural activity (ERNAs). See, e.g., Sinclair, et al., "Subthalamic Nucleus Deep Brain Stimulation Evokes Resonant Neural Activity," Ann. Neurol. 83(5), 1027-31, 2018. The ERNA responses typically have an oscillation frequency of about 200 to about 500 Hz and amplitudes of about 20 to about 200 μV. Stimulation of the STN, and particularly of the dorsal subregion of the STN, has been observed to evoke strong ERNA responses, though ERNA may be detected in other anatomical brain structures, as discussed in more detail below. Thus, ERNA can provide a biomarker for electrode location, which can potentially indicate acceptable or perhaps optimal lead placement and/or stimulation field placement for achieving the desired therapeutic response. FIG. 8A illustrates an example of an ERNA epoch after filtering 802 and after down-sampling 804 and removal of the residual stimulation artifact. FIG. 8B illustrates an example of an idealized ERNA in isolation. The ERNA comprises several positive peaks $P_n$ and negative peaks $N_n$, which may have one or more characteristic amplitudes, lengths, separations, latencies, or other features. The ERNA signal may decay according to a characteristic decay function F. Such oscillatory evoked neural responses may also be referred to as DBS Local Evoked Potentials (DLEPs) and/or Evoked Oscillating Neural Responses (EONRs) or other terms. The term ERNA will be used in this disclosure to refer to oscillatory evoked neural potentials in the patient's brain that are synchronized with stimulation, such as those illustrated in FIGS. 8A and 8B. It will be appreciated that the term ERNA refers to such signals, whether or not the signals are "resonant" in the strictest mathematical or physiological sense. More generally, such evoked neural responses in the patient's brain may simply be referred to as evoked neural responses and/or evoked potentials (EPs).

Figure 9:
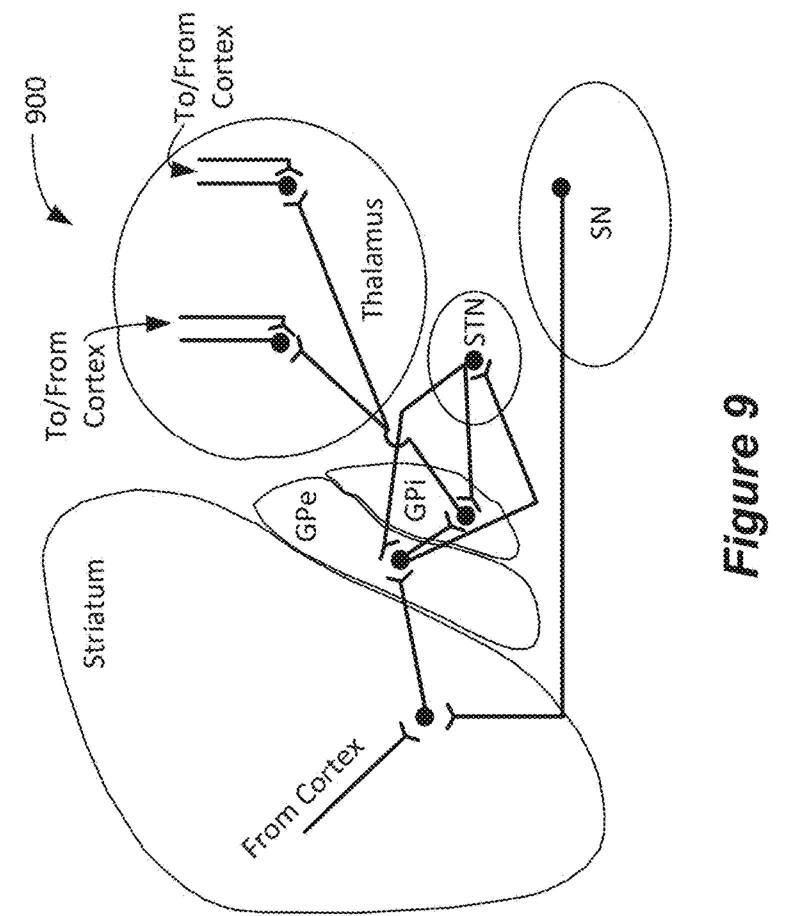
FIG. 9 schematically illustrates neuronal connections within anatomical brain structures.

ERNA is believed to arise from the reciprocal neural connections between the STN and other anatomical brain structures, such as the globus pallidus externus (GPe) and the globus pallidus internus (GPi). FIG. 9 shows a schematic 900 illustrating neural circuitry of the basal ganglia. The schematic shows synaptic connections within the STN, GPi, GPe, substantia nigra (SN), striatum, and thalamus. It should be noted that other anatomical brain structures that may be implicated in DBS therapy have been omitted from FIG. 9 for clarity. Such structures include in internal capsule (IC), zona incerta (ZI), optic tract (OT), and others. Since the various anatomical brain structures differ in their reciprocal neural connections with the STN, ERNA signals recorded in the differing brain structures may differ from one another as to their oscillation frequency, relative timing, etc.

Accordingly, one aspect of the instant disclosure relates to using ERNA as a biomarker for determining or estimating the position of an electrode lead implanted in a patient's brain. For example, the EPs, such as ERNA may be used to estimate the absolute position of the electrode lead and/or to estimate or confirm the location(s) of the various electrode contacts, for example, vis-à-vis their location within a given anatomical brain structure. In some embodiments, the electrophysical techniques may be used to determine which anatomical brain structure (i.e., which physiologically distinct brain region) a particular electrode contact is located in, and/or to confirm if various electrodes are located within the same anatomical brain structure. As used herein, the term "anatomical brain structure" includes physiologically distinct regions of the brain, whether are not those regions are anatomically distinguishable using common clinical tools. As mentioned above, lead placement in DBS and determining the location of the electrode lead is typically assisted using a variety of imaging techniques, such as pre-operative MRI and pre- and/or post-operative CT. Such images are acquired, processed, and segmented to provide an estimate of various neural target structures within the brain as a guide to the lead's placement with respect to the target structures, such as the STN, GPi, etc., which may be indicated on the processed images. A representation of the lead may be overlayed upon the processed images and used to assist placement, programming, and the like. However, often the images may lack the resolution to provide the desired precision in the lead's location. Also, the brain may shift between the time the images are acquired and the time the images are used to inform programming. For example, air may be introduced into the cranial cavity during the lead placement surgery, causing the brain to shift. The electrophysical techniques described herein may be used to augment the image-based lead location techniques presently used.

Figure 10:
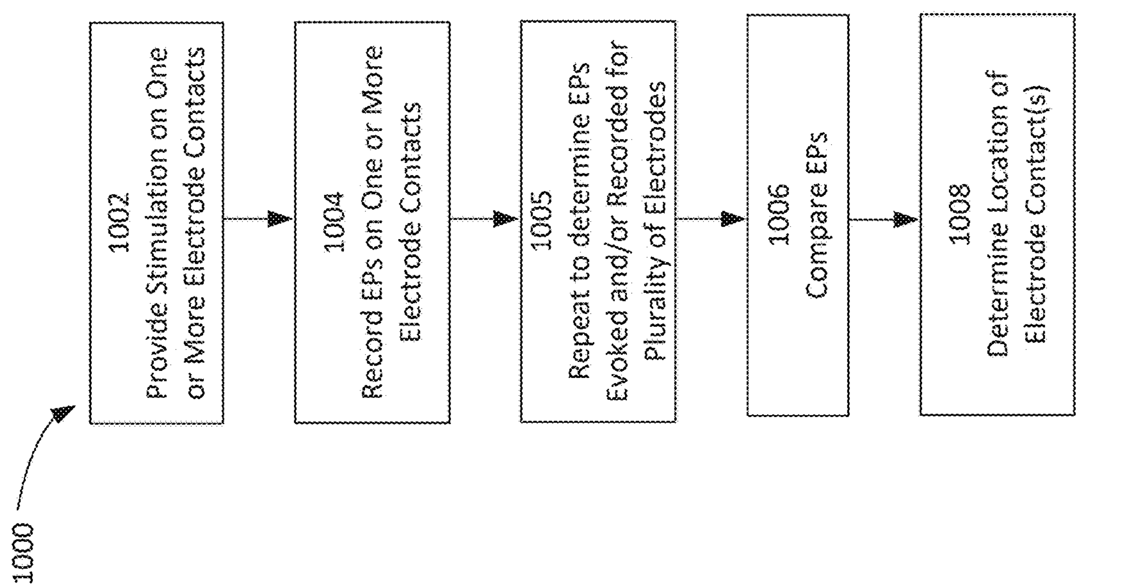
FIG. 10 illustrates an embodiment of a workflow for using EPs to estimate the location of an electrode lead within a patient's brain.

FIG. 10 illustrates an embodiment of a workflow 1000 for using electrophysical measurements to estimate or determine a location of an electrode lead within the brain of a patient. Assume that the electrode lead is positioned with the patient's brain. The workflow 1000 aims to determine which anatomic brain structure one or more of the electrode contacts on the lead are located in. At step 1002, one or more of the electrode contacts are used to provide stimulation that is configured to evoke EPs and at step 1004 one or more of the electrode contacts are used to record EPs evoked by the stimulation. Typically, the stimulation may be monopolar, but bipolar stimulation may also be used. The stimulation may be tonic or may be provided as bursts. According to some embodiments, bursts of about 10 to 20 pulses of stimulation at about 100 to 200 Hz may be provided, followed by a quiescent period of a few seconds, during which EPs may be measured. According to some embodiments, stimulation may be provided at one of the electrode contacts and then EPs may be recorded at that electrode contact and/or the other electrode contacts during the quiescent period. This method may be repeated using other electrode contacts as the stimulating and/or recording electrode contacts (Step 1005). At step 1006, EPs evoked by stimulation at different electrode contacts or recorded at different electrode contacts may be compared, and at step 1008 the comparison may be used to determine the location of the electrode contacts.

Figure 11A:
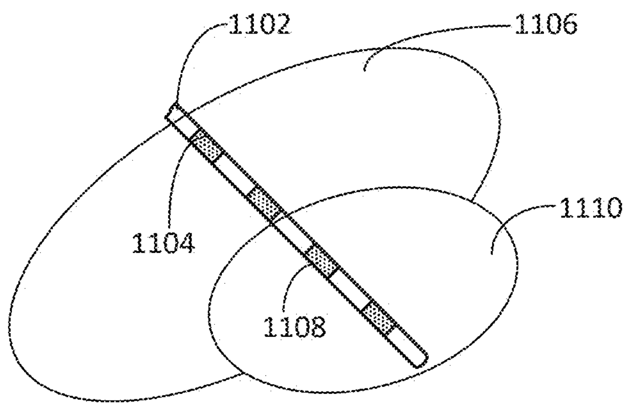
FIGS. 11A and 11B illustrate EPs evoked/recorded within different anatomical brain structures.

FIG. 11A schematically illustrates an embodiment of the electrophysical methods described herein. Assume that an electrode lead 1102 is implanted in a patient's brain, such that a first electrode contact 1104 is in a first anatomical brain structure 1106 (the GPe, for example) and a second electrode contact 1108 is in a second anatomical brain structure 1110 (the GPi, for example). The steps 1002-1005 of the workflow 1000 (FIG. 10) may be performed to determine EPs evoked and/or recorded for various of the electrode contacts on the electrode lead 1102. Since the electrode contacts 1104 and 1108 are each in different anatomical brain structures, and the different brain structures have different reciprocal neural connections and neural circuits, it is expected that the EPs evoked/recorded at the two electrodes will be different. For example, the EPs recorded in at the two different electrodes may have different relative timings, even if the EPs were evoked by stimulation at a single location. It should be noted that the electrode lead 1102 illustrated in FIG. 11A comprises ring electrode contacts. However, directional electrode contacts, such as the split ring contacts of the electrode lead 33 (FIG. 1B) may also be used.

Figure 11B:
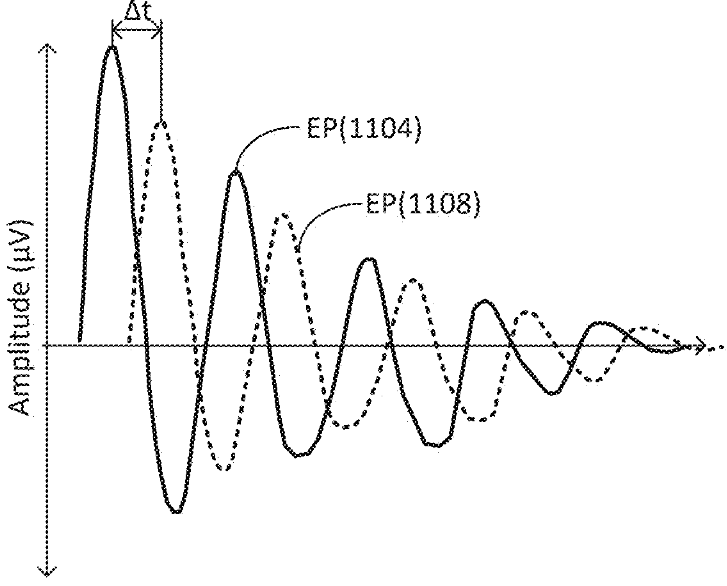

Referring to FIG. 11B, the trace EP (1104) represents an EP evoked/recorded at the electrode contact 1104 and the trace EP (1108) represents an EP evoked/recorded at the electrode contact 1108. Notice that EP (1108) is delayed an amount Δt with respect to the EP (1104). The frequencies of the two signals are also slightly different. These differences may arise because the two EP signals arise from different neural circuits having different neural connections. They may resonate with slightly different frequencies and exhibit different delays.

The differences in the EPs evoked and/or recorded in different anatomical brain structures, as illustrated in FIGS. 11A and 11B, may be used as a biomarker for providing information about the locations of stimulating and/or recording electrode contacts within the patient's brain. Examples of scenarios leveraging such biomarker information are described below.

According to some scenarios, assume that a clinician plans to implant an electrode lead such that a first one or more of the electrode contacts are in a first anatomical brain region (e.g., the GPe) and a second one or more of the electrode contacts are in a second anatomical brain region (e.g., the GPi). Since the first and second electrode contacts are to be in different anatomical brain regions, and as a consequence, may be involved in different neurological circuits and are thus physiologically different, the EPs evoked/recorded at those leads would be expected to be different. A priori knowledge of the neural circuitry of the two regions may be used to predict how the EPs of the two electrode contacts should differ. During the implantation procedure, the clinician may obtain recordings of EPs evoked/recorded at the first and second electrode contacts and use those EPs to guide/confirm implantation.

Figure 12:
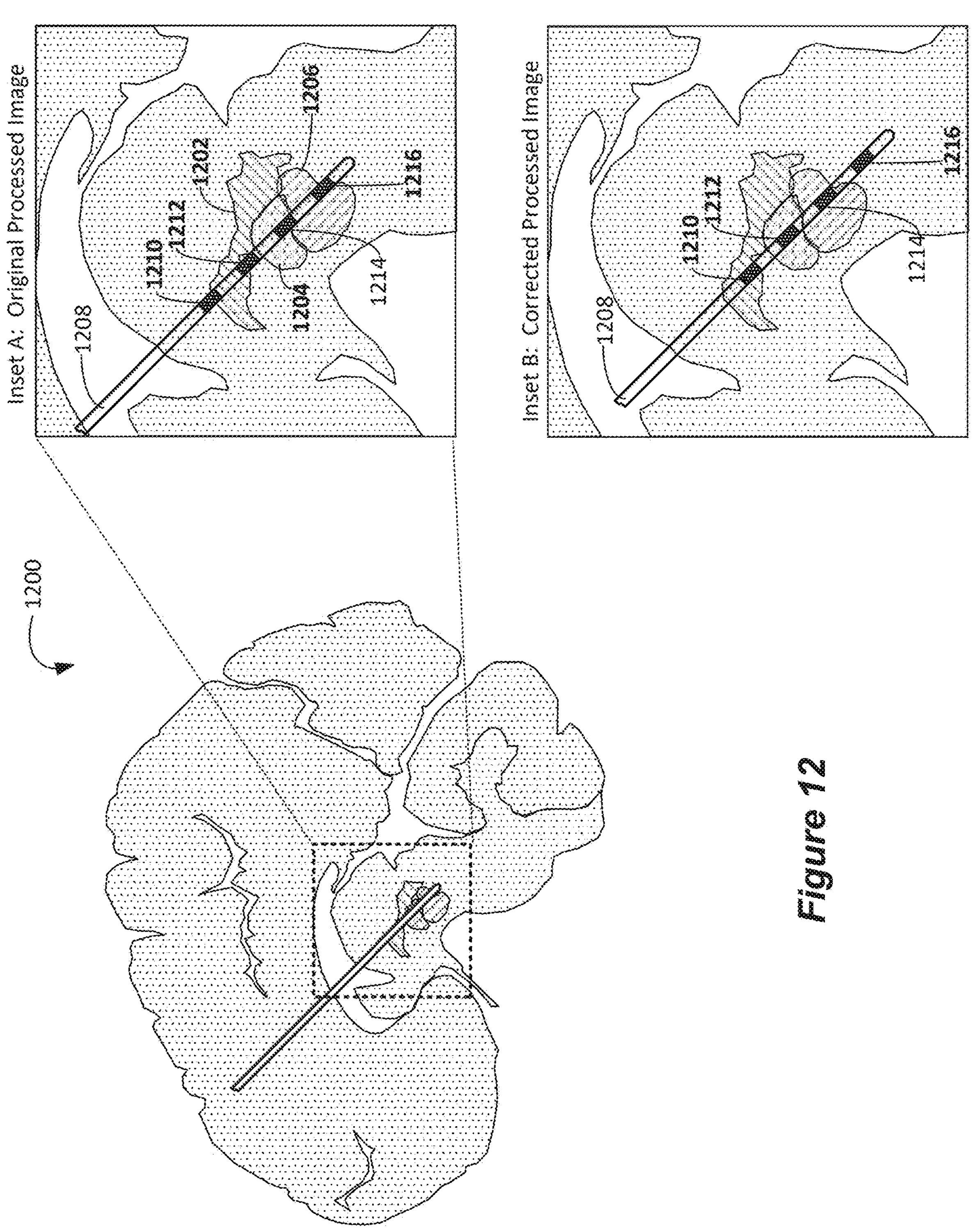
FIG. 12 illustrates an image showing a location of an electrode lead within a patient's brain.

Another scenario may involve using the electrophysiology measurements described above to confirm and/or correct lead placement vis-à-vis imaging data. FIG. 12 illustrates processed imaging data 1200, as may be displayed on a GUI following lead implantation. For example, the imaging data may be displayed on a GUI 100 (FIG. 7) on a clinician programmer (CP) 70 (FIG. 5), as discussed above. As is known in the art, such imaging data may be processed to provide a representation of various anatomical brain regions, such as brain regions 1202, 1204, and 1206. The processed image data also includes a representation 1208 of an electrode lead. In the original processed image (Inset A), the location of the electrode lead may be based on the surgical plan executed during the implantation surgery, for example. The estimated location of each of the electrode contacts, 1210, 1212, 1214, and 1216 with respect to the various anatomical brain regions is based on that presumed position of the electrode lead. But as mentioned above, the processed imaging data may not be absolutely correct, for a variety of reasons. The electrophysical measurements described above can be used to confirm/correct the positioning of the representation of the electrode lead and or the positioning and representation of the anatomy, including by adjusting the size, shape location of an anatomically segmented region. The latter is performed in particular as the geometry of the lead is more reliably known, and so when anatomy and physiology differ, physiology may at time or in certain conditions be weighted further when adjusting the underlying model. For example, EPs evoked and/or recorded at each of the electrode contacts 1210, 1212, 1214, and 1216. For example, the relative delays, frequencies, etc., of the EPs evoked and/or recorded at each of the contacts may suggest that the contact 1210 is located within the anatomical brain region 1202, contact 1212 is located within the anatomical brain region 1204, contact 1214 is located within the anatomical brain region 1206, and contact 1216 is located within none of those anatomical brain regions. The location of the representation of the electrode lead 1208 may be repositioned with respect to the imaging data to reflect the knowledge gained from the electrophysical measurements. This updated knowledge may be used for programming and/or optimizing the programming of the therapeutic stimulation for the patient, as described above.

Aspects of the disclosure relate to using evoked/recorded EPs to inform the programming of therapeutic stimulation for the patient. According to some embodiments, the EPs may be used to determine (or suggest) a range or value of frequency, timing, rate, and/or other waveform or stimulation parameters for the therapeutic stimulation. As mentioned above, the oscillating EPs described herein are believed to arise from resonant activity supported by reciprocal neural connections within and among various anatomical brain regions. According to some embodiments, stimulation with frequencies and timings that modulate such activity may be particularly effective at treating the patient's symptoms. According to some embodiments, an algorithm or transfer function may be used to determine or suggest a stimulation frequency based on one or more characteristics of recorded EPs. Such an algorithm/transfer function receives one or more characteristics of the recorded EPs as an input, and provides a suggestion for a stimulation frequency as an output. According to some embodiments, such algorithms/transfer functions may be provided within an external computing device, such as the CP 70 (FIG. 5). For example, the algorithm/transfer function(s) may be stored in non-volatile memory and executed using one or more processers of the computing device.

Figures 13, 14:
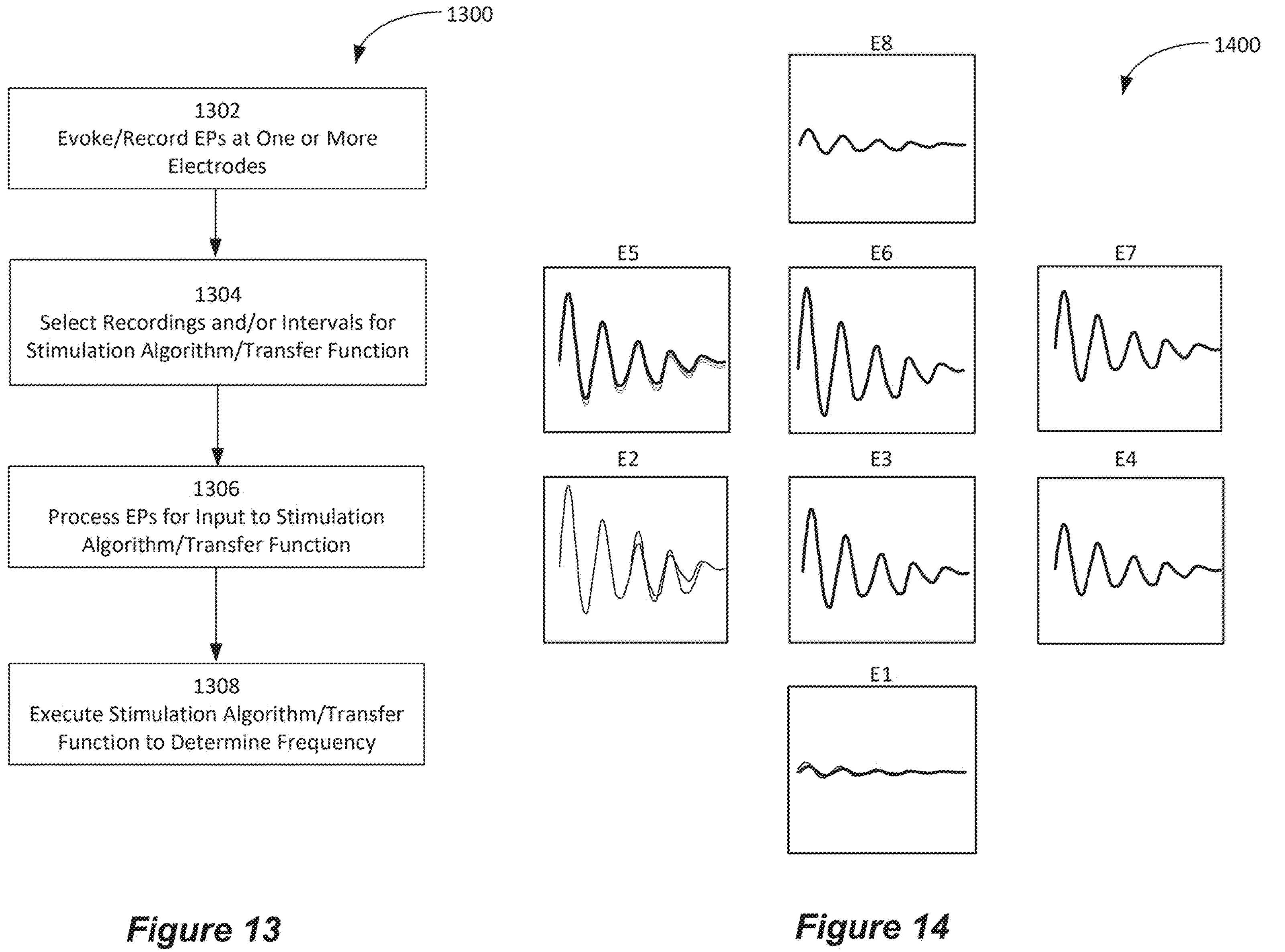
FIG. 13 illustrates an embodiment of a workflow for using EPs to inform the selection of a rate/frequency for therapeutic stimulation.
FIG. 14 illustrates an array of electrodes overlayed with a representation of EPs evoked/recorded at the electrodes.

Aspects of the disclosure relate to determining which EPs and/or which characteristics of EPs to provide as input for such algorithms/transfer functions. FIG. 13 illustrates an embodiment of a workflow 1300 for using EPs to inform the selection of an appropriate stimulation frequency. At step 1302, EPs are evoked and/or recorded using one or more of the electrodes of an electrode lead implanted within the patient's brain. As explained above, one of the electrode contacts may be used to provide stimulation configured to evoke EPs and the EPs may be recorded using that same electrode contact and/or other electrode contacts of the stimulation lead. The stimulation/recording steps may be repeated for others of the electrode contacts.

Steps 1304 and 1306 involve selecting and processing EPs to use as input for an algorithm or transfer function that is configured to select or recommend a stimulation frequency based on properties of the recorded EPs. According to some embodiments, the EP(s) to use as inputs may be selected from the electrode contact that exhibits the strongest EP. FIG. 14 illustrates an array 1400 of electrodes laid out in a two-dimensional array. In the array 1400, the electrode contacts E1 and E8 are ring electrodes and the electrode contacts E2-E7 comprises directional (split-ring) electrodes. The electrodes of the array 1400 may be configured upon an electrode lead, such as the electrode lead 33 (FIG. 1B). The representations of the electrode contacts E1-E8 are overlayed with representations of traces of recorded EPs recorded at each of the electrodes. In the array 1400, the EP trace recorded at E6 appears to be the strongest, so, according to some embodiments, that EP trace might be chosen to provide the input to the algorithm/transfer function for suggesting a stimulation frequency. According to other embodiments, EPs recorded at any electrode contacts where the EP amplitude exceeds a threshold value may be averaged, including using weighted-averaging, where weights could be assigned proportionally to features, to provide the input. According to some embodiments, electrode contacts that are determined to be located within a particular anatomical brain structure may be used. According to some embodiments, only traces that meet certain selection criteria may be selected. For example, the selection criteria may comprise expected frequency ranges, etc. According to some embodiments, a single recorded trace may be used. According to other embodiments, multiple traces may be averaged, or otherwise combined. These multiple traces can be comprised of multiple presentations of the same evoking and recording configuration, including averages across space, averages across conditions, and combinations thereof. The EPs may be filtered, scaled, and/or other heuristics may be applied. According to some embodiments, noisy channels may be rejected based on one or more rejection criteria. According to some embodiments, signals that are rejected (or otherwise missing) may be interpolated or extrapolated from other channels/contacts.

According to some embodiments, the frequency or rate of the selected EP(s) may be used as input to the simulation algorithm/transfer function. The rate may be an instantaneous rate or an average of instantaneous rates. The rate may be determined at a particular time or time period during the EP or averaged over a time period. Various averaging techniques may be used, for example, skip-one rates, averages across repetitions, averaging across space/electrode contacts, etc. According to some embodiments, the selection methodology may be used to arrive at a single input for the algorithm/transfer function based on a plurality of recorded EPs are portions of EPs.

Once an appropriate EP or EPs have been selected and processed, the result may be used as the input to the stimulation algorithm/transfer function to select or suggest a rate/frequency for stimulation, and the algorithm/transfer function may be executed (Step 1308). According to some embodiments, the algorithm/transfer function may comprise using a fraction (e.g., one half, on quarter, etc.) of the EP frequency/rate. For example, if the processed rate from the EP is 350 Hz, then the algorithm/transfer function may suggest a stimulation frequency of 175 Hz. The scaling factor used may consider information regarding the anatomic location of the recording, evoking, or both electrode(s), and/or physiological information regarding the circuit location, such as which electrode(s) are located in the region that exhibits the oscillated earlier or later in phase. Suggested rates may be confirmed by presenting modified evoking stimuli, such as by varying the rate of evoking stimuli, at rates similar to or different than the proposed therapeutic stimuli. For example, if ERNA is detected at one location at 300 Hz, an initial proposed therapeutic stimulation frequency might be 125 Hz. Additional evoking stimuli might alter the ERNA frequency to 280 Hz, and a refined proposed therapeutic rate of 120 Hz could be proposed. Stimulation may then be provided using the suggested stimulation frequency. It should be noted that the frequency, rate and/or timing of the stimulation may be correlated with other measurements or recordings. For example, EPs recorded from other areas of the brain may be used to inform the rate, frequency, and/or timing. Likewise, recordings from cortical electrodes, EEG electrodes, and the like may be used. According to some embodiments, the rates may be determined from the EPs recorded from a first one or more electrode contacts, but the therapeutic stimulation may be applied at other electrode contacts. For example, the EPs recorded in the GPi may be used to provide input to the rate-determining algorithm/transfer function, but the therapeutic stimulation using the determined rate may be applied at one or more electrode contacts located in the GPe.

Figure 15:
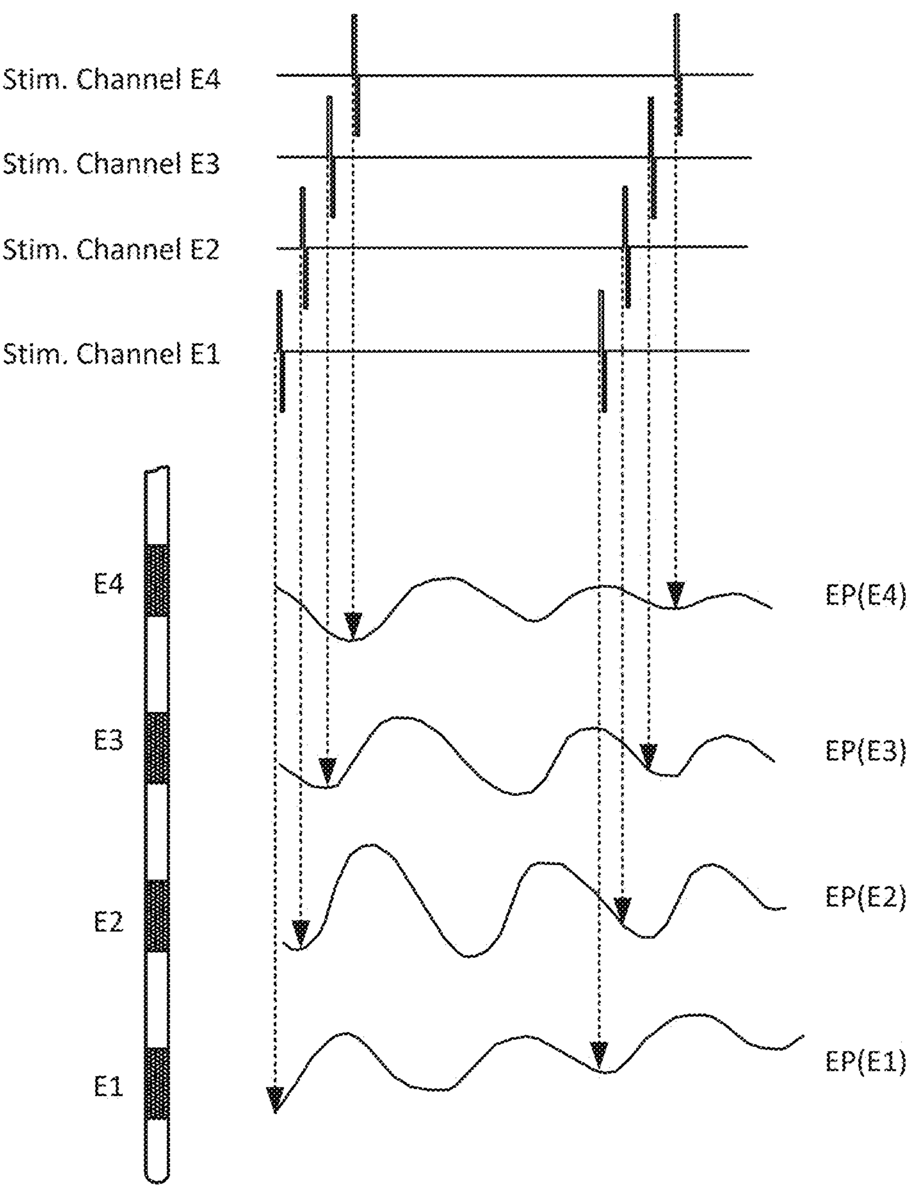
FIG. 15 illustrates an embodiment for using evoked/recorded EPs to inform timing of stimulation on multiple timing channels.

The relative frequencies and/or delays of EPs evoked and/or recorded at various electrode contacts may also be used to inform choices of the relative timing of stimulation that may be applied on different channels (for example, where the different channels correspond to different channels electrode contacts). FIG. 15 illustrates an electrode lead 1502 having four electrode contacts E1-E4. FIG. 15 also shows EPs recorded at each of those electrodes—EP(E1)-EP(E4), respectively. Notice that the EPs are delayed with respect to each other, i.e., they are out of phase. Their frequencies may be different as well. These differences may arise because of the relative positioning of each of the electrode contacts within the patient's brain, for example, if the different electrode contacts are located in different anatomical brain regions. According to some embodiments, the stimulation delivered at each of the electrode contacts may be configured to coincide with a predetermined time/location of the EP's waveform. For example, in FIG. 15 the timing channels are configured to deliver stimulation at every other trough of the electrode contact's corresponding waveform. This information might be used to suggest that therapeutic stimulation defined in two timing channels, sometimes called 'areas', having some fixed or variable timing offset (e.g., a stimulation rate or frequency dependent offset, or a fixed offset such as 100 ms) be combined into a single timing-channel or area. Conversely, the recommendation might be to stimulate two different anatomical or physiological (circuit) regions using different timing channels, and including adjusting the offset or delay between the two channels, e.g. from 100 ms to a longer offset which is calculated from a model of the circuit relationship between the two regions and a preferential delay in stimulation between the two designed to enhance therapeutic efficacy or reduce severity or occurrence of side effect.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of estimating a position of an electrode lead within a patient's brain, wherein the electrode lead comprises a plurality of electrodes, the method comprising:

using one or more of the plurality of electrodes to provide active stimulation to the patient's brain;

using at least a first of the plurality of electrodes to record first evoked potentials (EPs) evoked by the active stimulation and a second of the plurality of electrodes to record second EPs evoked by the active stimulation;

comparing the first EPs and the second EPs to determine a delay between the EPs wherein the delay is indicative a difference in a number or kind of synapses between a first neural circuit giving rise to the first EP and a second neural circuit giving rise to the second EP; and using the comparison to estimate a location of the electrode lead within the patient's brain.

2. The method of claim 1, wherein the first and second EPs comprise evoked resonant neural responses (ERNA).

3. The method of claim 1, wherein estimating a location of the electrode lead within the patient's brain comprises determining if the first and second electrodes are in different anatomical brain structures.

4. The method of claim 1, further comprising taking an action based on the estimated location of the electrode lead within the patient's brain.

5. The method of claim 4, wherein the action comprises moving the electrode lead or suggesting a move of the electrode lead.

6. The method of claim 4, wherein the action comprises suggesting or optimizing an electrode configuration, wherein the electrode configuration comprises one or more of the plurality of electrodes assigned to deliver therapeutic stimulation.

7. The method of claim 4, wherein the action comprises updating a prior estimate of the electrode lead's location within the patient's brain.

8. The system of claim 7, wherein the first and second EPs comprise evoked resonant neural responses (ERNA).

9. A system for estimating a position of an electrode lead within a patient's brain, wherein the electrode lead comprises a plurality of electrodes, the system comprising:

control circuitry configured to:

use one or more of the plurality of electrodes to provide active stimulation to the patient's brain;

use at least a first of the plurality of electrodes to record first evoked potentials (EPs) evoked by the active stimulation and a second of the plurality of electrodes to record second EPs evoked by the active stimulation;

compare the first EPs and the second EPs to determine a delay between the EPs wherein the delay is indicative a difference in a number or kind of synapses between a first neural circuit giving rise to the first EP and a second neural circuit giving rise to the second EP; and use the comparison to estimate a location of the electrode lead within the patient's brain.

10. The system of claim 9, wherein the first and second EPs comprise evoked compound action potentials (ERNA).

11. The system of claim 9, wherein estimating a location of the electrode lead within the patient's brain comprises determining if the first and second electrodes are in different anatomical brain structures.

12. The system of claim 9, further configured to take an action based on the location of the electrode lead within the patient's brain.

13. The system of claim 12, wherein the action comprises moving the electrode lead or suggesting a move of the electrode lead.

14. The system of claim 12, wherein the action comprises suggesting or optimizing an electrode configuration, wherein the electrode configuration comprises one or more of the plurality of electrodes assigned to deliver therapeutic stimulation.

15. The system of claim 12, wherein the action comprises updating a prior estimate of the electrode lead's location within the patient's brain.

16. The system of claim 15, wherein the updating comprises adjusting a location of a graphical representation of the electrode lead with respect to one or more graphical representations of imaging data using a graphical user interface (GUI).

17. A method of estimating a position of an electrode lead within a patient's brain, wherein the electrode lead comprises a plurality of electrodes, the method comprising:

using one or more of the plurality of electrodes to provide active stimulation to the patient's brain;

using at least a first of the plurality of electrodes to record first evoked potentials (EPs) evoked by the active stimulation and a second of the plurality of electrodes to record second EPs evoked by the active stimulation;

comparing the first EPs and the second EPs to determine if the first and second electrodes are concurrently in different anatomical brain structures; and using the comparison to estimate a location of the electrode lead within the patient's brain.

18. The method of claim 17, further comprising suggesting a move of the electrode lead based on the estimated location of the electrode lead within the patient's brain.

19. The method of claim 17, further comprising suggesting or optimizing an electrode configuration, wherein the electrode configuration comprises one or more of the plurality of electrodes assigned to deliver therapeutic stimulation based on the estimated location of the electrode lead within the patient's brain.

20. The method of claim 17, further comprising updating a prior estimate of the electrode lead's location within the patient's brain based on the estimated location of the electrode lead within the patient's brain.

* * * * *